United States Patent [19]

Hirai et al.

[11] 4,318,858
[45] Mar. 9, 1982

[54] THIOETHYLAMIDE DERIVATIVES

[75] Inventors: Kentaro Hirai, Kyoto; Shigeru Matsutani, Sakai; Teruyuki Ishiba, Takatsuki; Itsuo Makino, Kobe; Masami Doteuchi, Hirakata; Koichi Otani, Kawachinagano, all of Japan

[73] Assignee: Shionogi & Co., Ltd., Osaka, Japan

[21] Appl. No.: 212,222

[22] Filed: Dec. 2, 1980

[30] Foreign Application Priority Data

Dec. 7, 1979 [JP] Japan .................. 54-159510

[51] Int. Cl.³ .................. C07D 307/52; C07D 207/04; C07D 333/18; C07D 307/52
[52] U.S. Cl. .................. 260/347.2; 260/326.35; 260/326.36; 549/59; 549/60; 549/76; 542/416; 546/281; 546/284; 546/283; 424/263; 424/274; 424/275; 424/285
[58] Field of Search .......... 260/347.2, 326.35, 326.36; 549/76; 542/416

[56] References Cited

U.S. PATENT DOCUMENTS 4,128,658 12/1978 Price et al. .................. 260/347.2
4,239,769 12/1980 Price et al. .................. 260/326.35
4,264,614 4/1981 Clitherow et al. .............. 260/326.35

*Primary Examiner*—Henry R. Jiles
*Assistant Examiner*—Jane T. Fan
*Attorney, Agent, or Firm*—Wenderoth, Lind & Ponack

[57] ABSTRACT

A compound of the formula:

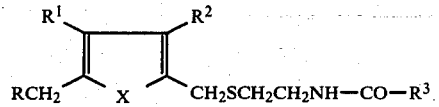

[wherein
R is dimethylamino or 1-pyrrolidinyl;
$R^1$ and $R^2$ each is hydrogen or $C_1$–$C_3$ alkyl;
$R^3$ is hydrogen, $C_1$–$C_3$ alkyl (optionally substituted by one member selected from the group consisting of cyano, $C_1$–$C_3$ alkoxy, phenyl, and 5- or 6-membered heterocyclic group), $C_3$–$C_6$ cycloalkyl, $C_2$–$C_5$ alkenyl (optionally substituted by one member selected from the group consisting of $C_1$–$C_3$ alkoxy, phenyl, and phenoxy), $C_6$–$C_{10}$ aryl (optionally substituted by one or two members selected from the group consisting of hydroxy, halogen, nitro, sulfamoyl, $C_1$–$C_3$ alkyl, $C_1$–$C_3$ alkoxy, $C_1$–$C_3$ alkanoyl, $C_2$–$C_4$ alkoxycarbonyl, $C_2$–$C_4$ dialkylamino, and $C_1$–$C_3$ alkanesulfonyl), or 5- or 6-membered heterocyclic group (optionally substituted by one member selected from the group consisting of oxo, halogen, $C_1$–$C_3$ alkyl, and $C_1$–$C_3$ alkoxy);
and X is oxygen or sulfur]
and its pharmaceutically acceptable acid addition salts is useful as histamine $H_2$ blockers.

4 Claims, No Drawings

THIOETHYLAMIDE DERIVATIVES

The present invention relates to compounds of the formula:

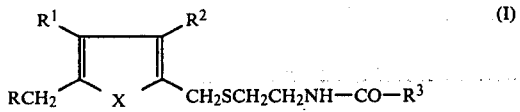

[wherein
R is dimethylamino or 1-pyrrolidinyl;
$R^1$ and $R^2$ each is hydrogen or $C_1$–$C_3$ alkyl;
$R^3$ is hydrogen, $C_1$–$C_3$ alkyl (optionally substituted by one member selected from the group consisting of cyano, $C_1$–$C_3$ alkoxy, phenyl, and 5- or 6-membered heterocyclic group), $C_3$–$C_6$ cycloalkyl, $C_2$–$C_5$ alkenyl (optionally substituted by one member selected from the group consisting of $C_1$–$C_3$ alkoxy, phenyl, and phenoxy), $C_6$–$C_{10}$ aryl (optionally substituted by one or two members selected from the group consisting of hydroxy, halogen, nitro, sulfamoyl, $C_1$–$C_3$ alkyl, $C_1$–$C_3$ alkoxy, $C_1$–$C_3$ alkanoyl, $C_2$–$C_4$ alkoxycarbonyl, $C_2$–$C_4$ dialkylamino, and $C_1$–$C_3$ alkanesulfonyl), or 5- or 6-membered heterocyclic group (optionally substituted by one member selected from the group consisting of oxo, halogen, $C_1$–$C_3$ alkyl, and $C_1$–$C_3$ alkoxy);
and X is oxygen or sulfur]
and their pharmaceutically acceptable acid addition salts.

More particularly, the present invention relates to compounds of the formula:

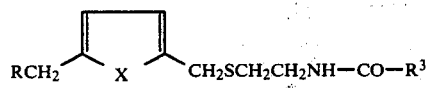

[wherein R, $R^3$ and X each has the same significance as defined above].

Concrete illustration of the terms used in the above definition is shown below:
alkyl includes methyl, ethyl, propyl, and isopropyl;
cycloalkyl includes cyclopropyl, cyclobutyl, cyclopentyl, cyclohexyl, etc.;
alkenyl includes vinyl, allyl, butenyl, butadienyl, pentadienyl, etc;
alkoxy includes methoxy, ethoxy, propoxy and isopropoxy;
alkoxycarbonyl includes methoxycarbonyl, ethoxycarbonyl and propoxycarbonyl;
alkanoyl includes formyl, acetyl and propionyl;
dialkylamino includes dimethylamino, diethylamino, methylethylamino and methylpropylamino;
alkanesulfonyl includes methanesulfonyl, ethanesulfonyl, propanesulfonyl, isopropanesulfonyl;
halogen includes fluorine, chlorine, bromine, iodine, etc.; aryl includes phenyl, naphthyl, etc.; 5- or 6-membered hetrocyclic ring includes furyl, thienyl, pyridyl, morpholinyl, pyrrolidinyl, etc.

The pharmaceutically acceptable acid addition salts includes those of inorganic acids (e.g. hydrochloric acid, hydrobromic acid, hydroiodic acid, sulfuric acid, nitric acid, phosphonic acid) and organic acids (e.g. acetic acid, citric acid, oxalic acid, lactic acid, succinic acid, tartaric acid, mandelic acid, methanesulfonic acid).

As this type of histamine $H_2$ blocker, cimetidine is dissolved in G. J. Durant, C. R. Ganellin, et al., J. Med. Chem., Vol. 20, 901 (1977; U.S. Pat. Nos. 3,876,647; 3,897,444 and 3,975,530.

An object of the present invention is to provide the novel thioethyl-amide derivatives (I) showing excellent histamine $H_2$ blocking activity.

The objective compounds (I) of the present invention are prepared according to the following scheme:

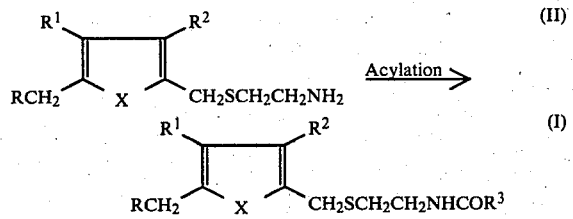

(wherein R, $R^1$, $R^2$, $R^3$ and X have each the same significance as defined above).

Thus the compounds (I) are prepared by reacting the starting amines (II) with an acylating agent containing a moiety of $R^3CO$—. This acylation may be performed appropriately in a conventional manner such as by the acid anhydride prorcess, acid chloride process, acid/DCC process or acid/triphenylphosphine process. Illustrative embodiments of the acylation adopted in the present invention are shown as follows:

(a) Acid anhydride process:
Amine (II) is reacted with the corresponding acid anhydride, or mixed anhydride e.g. $(R^3CO)_2O$, $R^3COOCOC_2H_5$. The reaction is conducted in an appropriate solvent, e.g. pyridine, at room temperature or under heating up to reflux temperature.

(b) Acid chloride process:
Amine (II) is reacted with the corresponding acid chloride $R^3COCl$ in the presence of an acid removing agent such as pyridine, triethylamine, HMPA, which also works as a solvent. The reaction is conducted at room temperature or under cooling or heating.

(c) Acid/DCC process:
Amine (II) is reacted with the corresponding free acid $R^3COOH$ in the presence of DCC (dicyclohexylcarbodiimide) in an appropriate solvent such as dichloroethane, chloroform, ether, dimethylformamide or dimethylsulfoxide at room temperature or under heating.

(d) Acid/triphenylphosphine/disulfide process:
Amine (II) is reacted with the corresponding free acid $R^3COOH$ in the presence of triphenylphosphine and a disulfide (e.g. 2,2'-bis(N-methylformamidophenyl)disylfide, 2,2'-dipyridyl disulfide). The reaction may be performed in a solvent like acetonitrile.

The starting amines (II) may be prepared according to the following scheme:

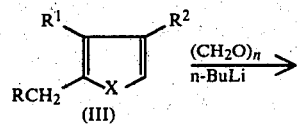

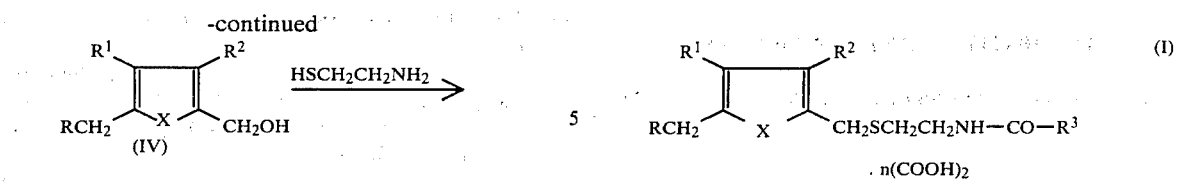

(wherein R, R¹ and R² each has the same significance as defined above).

Thus the compounds (II) can be prepared by reacting the compounds (III) with paraformaldehyde $(CH_2O)_n$ in the presence of butyl lithium n-BuLi and reacting the resulting alcohols (IV) with 2-mercaptoethylamine in the presence of conc. hydrochloric acid as a condensing agent.

The compounds (I) of the present invention and their pharmaceutically acceptable acid addition salts bind the active site of the histamine $H_2$ receptor in competition with histamine to show a histamine $H_2$ blocking activity. In Table 1 the $pA_2$ column shows the degree of inhibiting the palpitation number of guinea pig's enucleated atrium by the compounds (I) (the oxalates).

TABLE 1

| Test No. | R | R¹ | R² | R³ | X | n | $pA_2$ |
|---|---|---|---|---|---|---|---|
| 1 | $(CH_3)_2N-$ | H | H | phenyl | O | 1 | 6.19 |
| 2 | " | " | " | pyridyl | " | 2.5 | 6.08 |
| 3 | " | " | " | thienyl | " | 1 | 6.17 |
| 4 | " | " | " | phenyl-COOCH₃ | " | 0 | 6.33 |
| 5 | " | " | " | $-CH=CH-CH=CH-CH_3$ | " | 1 | 5.72 |
| 6 | " | " | " | $-H$ | " | 1.5 | 5.73 |
| 7 | " | " | " | phenyl-SO₂NH₂ | " | 1 | 6.82 |
| 8 | pyrrolidinyl | H | H | phenyl-COOCH₃ | S | 1 | 6.26 |
| 9 | " | " | " | phenyl-NO₂ | " | 1 | 6.04 |
| 10 | " | " | CH₃ | H | phenyl-SO₂NH₂ | " | 0 | 5.66 |
| 11 | " | " | H | $-CH(CH_3)_2$ | pyridyl | " | 1.5 | 6.30 |
| 12 | " | " | CH₃ | H | phenyl-NO₂ | O | 1 | 6.07 |
| 13 | Cimetidine | | | | | | 6.63 |

Note:
The $pA_2$ value is defined as a negative logarithm of the concentration of the compound (I) required to shift the dose-response of histamine to the high concentration side by 2-fold. [Ariens, E.J., Molecular Pharmacology, 1 (1964), Academic Press, New York and London].

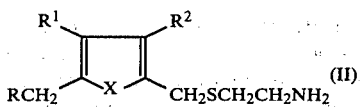

Further N-[2-[[(5-dimethylaminomethyl-2-furyl)-methyl]thio]ethyl]-4-sulfamoylbenzamide oxalate showed $ED_{50}$ 2.54 mg/kg in the gastric acid secretion inhibiting activity tested in Donryu male rats, in which the antagonism to histamine was confirmed by measuring the pH value in the stomach; acute toxicity $LD_{50}$ 150 mg/kg i.v. and above 1,000 mg/kg p.o. in mice. Other compounds also showed similar activities.

Accordingly the compounds (I) of the present invention showing powerful histamine $H_2$ inhibition are useful as remedies for diseases to be alleviated by inhibiting the histamine $H_2$ activity, for example, gastric ulcers.

The compounds (I) of the present invention or their pharmaceutically acceptable acid addition salts may be orally or parenterally administered. In using as an injection, the compounds (I) may be administered in the form of aqueous solution by conventional techniques such as intravenous, intramuscular or subcutaneous administration. The compounds (I) may be sealed in ampoules in the form of a solution but may preferably be preserved as crystals, fine crystals or lyophilisates in ampoules or vials and dissolved in water immediately before use.

Furthermore, the compounds (I) or their pharmaceutically acceptable acid addition salts may be formulated into external or internal preparations in combination with pharmaceutically acceptable additives such as diluents (e.g., starch, sucrose, lactose, calcium carbonate, kaolin), fillers (e.g. lactose, starch, calcium phosphate, kaolin, bentonite, or talc), lubricants (e.g. stearic acid, sodium benzoate), and the like. Such formulations include solutions, suspensions, powders, granules, capsules, tablets, injections, emulsions and suppositories, and these preparations may be prepared in a conventional manner for pharmaceutical practice. An appropriate daily dosage of the compounds (I) is ordinarily in 2–40 mg/kg body weight at 2 to 3 divided doses for treating patients suffering from peptic ulcer. However, such a dosage may be increased or decreased appropriately depending upon the symptoms, histories, ages, and sexes of the patients.

Presently preferred and practical embodiments of the present invention are illustratively shown in the following examples.

EXAMPLE 1

Preparation of N-[2-[[(5-dimethylaminomethyl-2-furyl)methyl]thio]ethyl]-2-thiophenecarbonamide:

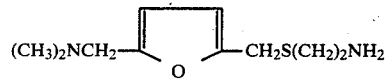
1

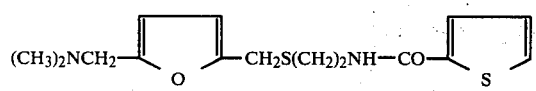
2

To a solution of Compound 1 (0.428 g) in HMPA (2 ml) is added 2-thenoyl chloride (0.322 g) under ice-cooling and the resultant mixture is stirred at room temperature for 2 hours and allowed to stand overnight. The reaction mixture is neutralized with aqueous sodium hydrogencarbonate and shaken with ether. The organic layer is washed with water, dried and concentrated. The residue is purified by chromatography on a column of silica gel/methanol to give Compound 2 as an oil. NMR, $\delta CDCl_3$: 2.27 (6H), 3.45 (2H), 3.80 (2H), 6.77 (1H, br.), 6.18 (2H)

The product is treated with an oxalic acid/ethanol solution and then with ether to give the oxalate of Compound 2 (0.51 g). mp 117°–118° C. (dec.) (recrystallized from ethanol). Anal. Calcd. for $C_{15}H_{20}N_2O_2S_2 \cdot (COOH)_2$: C, 49.26; H, 5.35; N, 6.76; S, 15.47. Found: C, 49.27; H, 5.41; N, 6.71; S, 15.44.

EXAMPLES 2–12

The reaction is performed as in Example 1 using Compound 1, whereby the following products (Ia) are obtained:

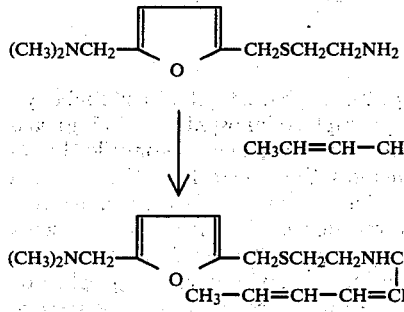

| Example No. | $R^3$ | n | mp(°C.) | Yield (%) |
|---|---|---|---|---|
| 2 | ⟨N⟩ | 2.5 | 152–154 d. | 57.0 |
| 3 | CH₃COO–⟨O⟩– | 0 | 77–79 | 82.0 |
| 4 | CH₂=CH– | 0 | oil | — |
| 5 | CH₃O–⟨O⟩– | 1 | 104–114 d. | 70.8 |
| 6 | ⟨OO⟩ | 1 | 134–135 d. | 67.0 |
| 7 | ⟨O⟩–OCH₂– | 1 | 112–114 d. | 40.3 |
| 8 | Cl–⟨O⟩– | 1 | 103–106 d. | 73.7 |
| 9 | ⟨O⟩–CH=CH– | 1 | 122–125 d. | 24.6 |
| 10 | ▷– | 1 | 75–78 d. | 24.5 |
| 11 | CH₃– | 0 | oil | — |
| 12 | ⟨O⟩– | 1 | 131–133 | 67.4 |

Note: d. means decomposition.

EXAMPLE 13

(CH₃)₂NCH₂–[furan]–CH₂SCH₂CH₂NH₂   1

↓ CH₃CH=CH–CH=CHCOOH (CH₃)₂NCH₂–[furan]–CH₂SCH₂CH₂NHCO–CH=CH–CH=CH–CH₃   3

To a solution of Compound 1 (0.428 g) and sorbic acid (0.225 g) in chloroform (10 ml) is added DCC (0.413 g) and the resultant mixture is stirred at room temperature for 1.5 hours. The reaction mixture is allowed to stand overnight and the precipitate is filtered off. The filtrate is concentrated, and the residue is chromatographed on a column of silica gel/methanol to give Compound 3 as an oil.

NMR $\delta CDCl_3$: 1.83 (d., J=5, 3H), 2.25 (6H), 3.43 (2H), 3.73 (2H), 6.15 (2H)

The product is treated with oxalic acid/ethanol solution and then with ether to give the oxalate of Compound 3 (0.4 g). Yield is 50%. mp. 95°–97° C.(d.) (recrystallized from ethanol).

Anal. Calcd. for $C_{16}H_{24}N_2SO_2 \cdot (COOH)_2 \cdot \frac{1}{2}H_2O$: C, 53.65; H, 6.63; N, 6.95; S, 7.96. Found: C, 53.56; H, 6.71; N, 6.81; S, 7.61.

EXAMPLES 14–15

The reaction is performed as in Example 13 using Compound 1, whereby the following products are obtained.

(CH₃)₂NCH₂—[furan]—CH₂SCH₂CH₂NH—CO—R³ · n(COOH)₂

| Example No. | R³ | n | mp (°C.) | Yield (%) |
|---|---|---|---|---|
| 14 | H | 1.5 | 110–113 d. | 80.6 |
| 15 | CN—CH₂— | 1 | 140–142 d. | 62.8 |

EXAMPLE 16

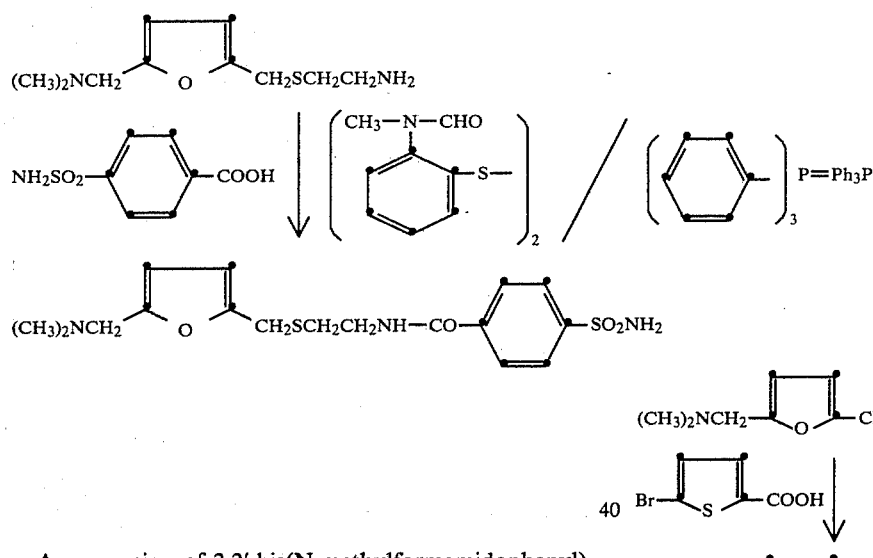

A suspension of 2,2'-bis(N-methylformamidophenyl) disulfide (0.997 g), triphenylphosphine (0.715 g) and 4-sulfamoylbenzoic acid (0.604 g) in acetonitrile (15 ml) is stirred for 70 minutes. Compound 1 (0.643 g) is added to the suspension, which is stirred at room temperature for 2 hours. The reaction mixture is allowed to stand overnight and the precipitate is filtered off. The filtrate is concentrated and the residue is chromatographed on a column of silica gel/methanol to give Compound 4 as an oil.

NMR, $\delta CDCl_3$: 2.13 (6H), 3.32 (2H), 3.68 (2H), 4.08 (br., 2H), 6.08 (2H), 7.40 (br., 1H), 7.70 (4H)

The product is treated with oxalic acid/ethanol and then with ether to give the oxalate of Compound 4 (0.93 g).

Yield is 63.7%. mp. 126°–128° C. (d.).

Anal. Calcd. for $C_{17}H_{23}N_3O_4S_2 \cdot (COOH)_2$: C, 46.81; H, 5.17; N, 8.62; S, 13.15. Found: C, 46.74; H, 5.09; N, 8.48; S, 13.19.

The reaction is performed similarly using 2,2'-dipyridyl disulfide in lieu of 2,2'-bis(N-methylformamidophenyl) disulfide. Yield is 57.2%.

EXAMPLES 17–18

The reaction is performed as in Example 16 using Compound 1, whereby the following products are obtained:

(CH₃)₂NCH₂—[furan]—CH₂SCH₂CH₂NH—CO—R³

| Example No. | R³ | Appearance | NMR $\delta^{CDCl_3}$ |
|---|---|---|---|
| 17 | [β-lactam] | oil | 2.23 (6H), 3.40 (2H), 3.70 (2H), 6.10 (2H) |
| 18 | [β-lactone] | oil | 2.25 (6H), 3.42 (2H), 3.75 (2H), 6.12 (2H) |

EXAMPLE 19

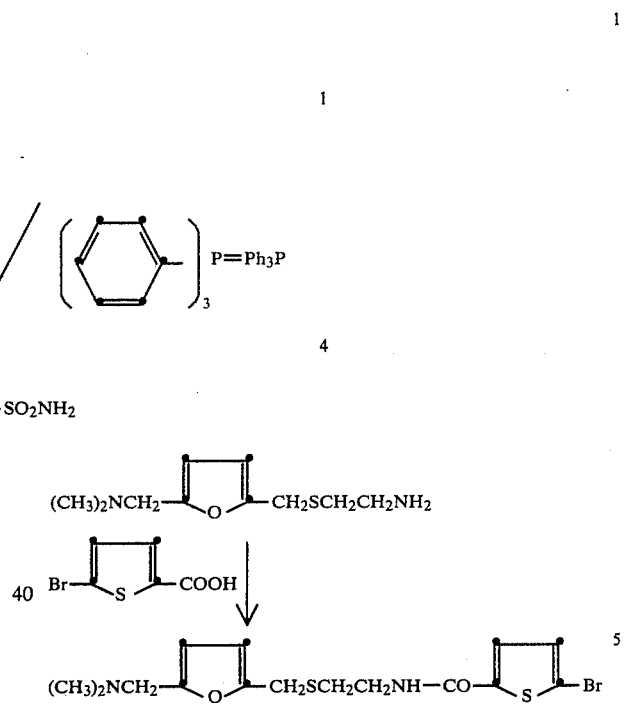

To a solution of 5-bromothiophene-2-carboxylic acid (0.977 g) in HMPA (5 ml) and acetonitrile (0.5 ml) cooled at −10° C. is added thionyl chloride (0.28 ml) and the resultant mixture is stirred at the same temperature for 20 minutes. Compound 1 (0.643 g) is added to the mixture, which is stirred at room temperature for 3 hours and allowed to stand overnight. The reaction mixture is neutralized with aqueous sodium hydrogencarbonate and shaken with ethyl acetate. The organic layer is washed with water, dried and concentrated. The residue is chromatographed on a column of silica gel/methanol, and the eluate is concentrated to give an oil. The oil is treated with oxalic acid/ethanol and then with ether to give the oxalate of Compound 5 (0.81 g).

Yield is 55%. mp. 133°–135° C. (d.).

Anal. Calcd. for $C_{15}H_{19}N_2O_2S_2Br \cdot (COOH)_2$: C, 41.38; H, 4.29; N, 5.68; S, 13.00; Br, 16.19. Found: C, 41.30; H, 4.20; N, 5.70; S, 12,78; Br, 16.55.

EXAMPLES 20–22

The reaction is performed as in Example 19 using Compound 1, whereby the following products are obtained.

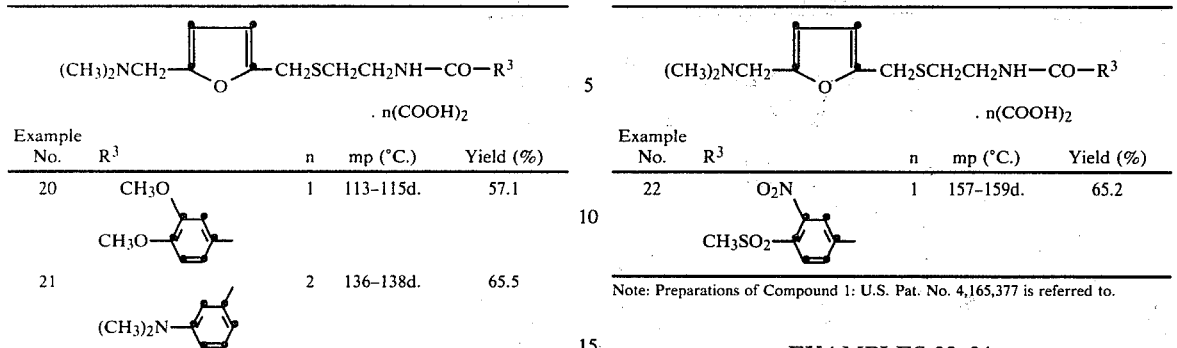

| Example No. | R³ | n | mp (°C.) | Yield (%) |
|---|---|---|---|---|
| 20 | CH₃O—/CH₃O—C₆H₃— | 1 | 113–115d. | 57.1 |
| 21 | (CH₃)₂N—C₆H₄— | 2 | 136–138d. | 65.5 |
| 22 | O₂N—/CH₃SO₂—C₆H₃— | 1 | 157–159d. | 65.2 |

Note: Preparations of Compound 1: U.S. Pat. No. 4,165,377 is referred to.

EXAMPLES 23–34

Compounds (Ib) are prepared from Compound 6 below according to the respective processes:

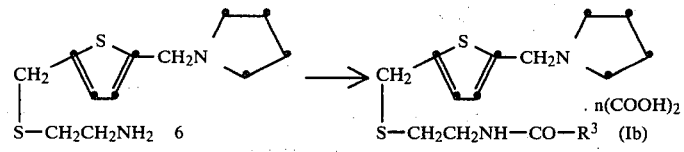

| Example No. | R³ | n | mp (°C.) | Yield (%) | Process |
|---|---|---|---|---|---|
| 23 | H— | 1 | 145–146 | 93 | c |
| 24 | CH₃— | 1 | oil | 91 | a |
| 25 | C₆H₅— | 1 | 130–131.5 | 85 | b |
| 26 | C₆H₅—OCH₂— | 1 | oil | 91 | " |
| 27 | CH₃OCO—C₆H₄— | 1 | 156–157 | 92 | " |
| 28 | pyridyl | 1 · ½H₂O | 135–137d | 99 | " |
| 29 | thienyl | 1 | 138–139 | 42 | " |
| 30 | CH₃O—C₆H₄— | 1 | 146–147 | 58 | " |
| 31 | O₂N—C₆H₄— | 1 | 133–135 | 94 | d |
| 32 | H₂NSO₂—C₆H₄— | 1 | oil | 64 | " |
| 33 | CH₃—CH=CH—CH=CH— | 1 | " | 99 | " |
| 34 | S—S⟩(CH₂)₄— | 1 | " | 80 | " |

Note: Compound 6 is prepared according to the following route:

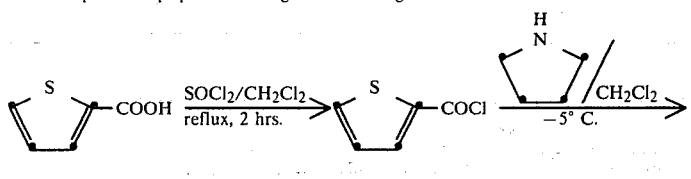

-continued

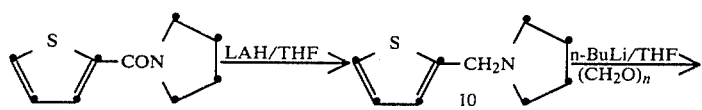

Mono-oxalate, mp 74–75° C.
9
bp$_7$ 87–89° C.
Mono-oxalate, mp 150–151° C.

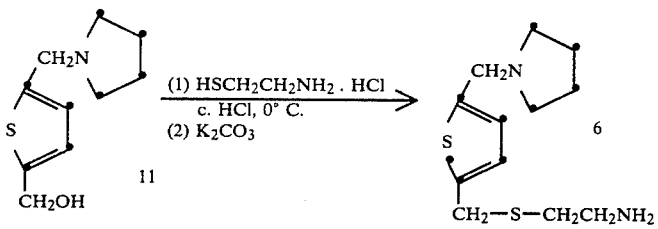

11
6
(Belg. pat. 867,105)

LAH = lithium aluminum hydride
THF = tetrahydrofuran

EXAMPLES 35–45

The products (Ic) are prepared from the following Compound 12 according to the respective processes.

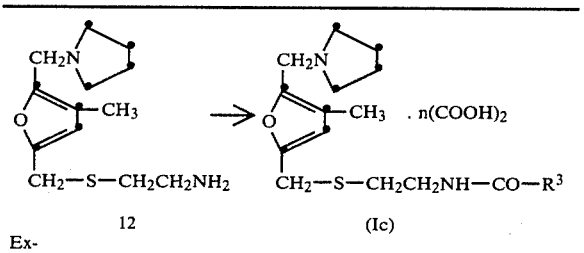

12
(Ic)

| Example No. | R³ | n | np (°C.) | Yield (%) | Process |
|---|---|---|---|---|---|
| 35 | H | 1 | 101–102 | 57 | c |
| 36 | CH₃— | 1 | oil | 70 | a |
| 37 | ⟨phenyl⟩ | 1 | " | 40 | b |
| 38 | ⟨C₆H₅—OCH₂—⟩ | 1 | " | 56 | " |
| 39 | CH₃OCO—⟨phenyl⟩— | 1 | 164–165 | 48 | " |
| 40 | ⟨pyridyl⟩ | 1 | 112–114 | 38 | " |
| 41 | ⟨thienyl⟩ | 1 | oil | 29 | " |
| 42 | CH₃O—⟨phenyl⟩— | 1 | " | 34 | " |
| 43 | O₂N—⟨phenyl⟩— | 1 | 165–166d. | 63 | d |
| 44 | H₂NSO₂—⟨phenyl⟩— | 1 | oil | 65 | " |
| 45 | CH₃CH=CH—CH=CH— | 1 | " | 80 | " |

Compound 12 is prepared according to the following route:

-continued

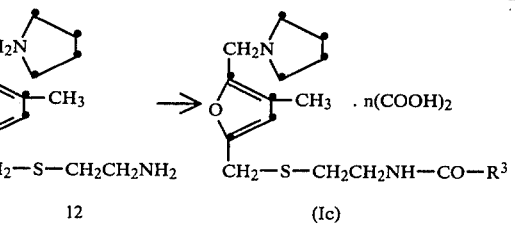

12
(Ic)

| Example No. | R³ | n | np (°C.) | Yield (%) | Process |
|---|---|---|---|---|---|

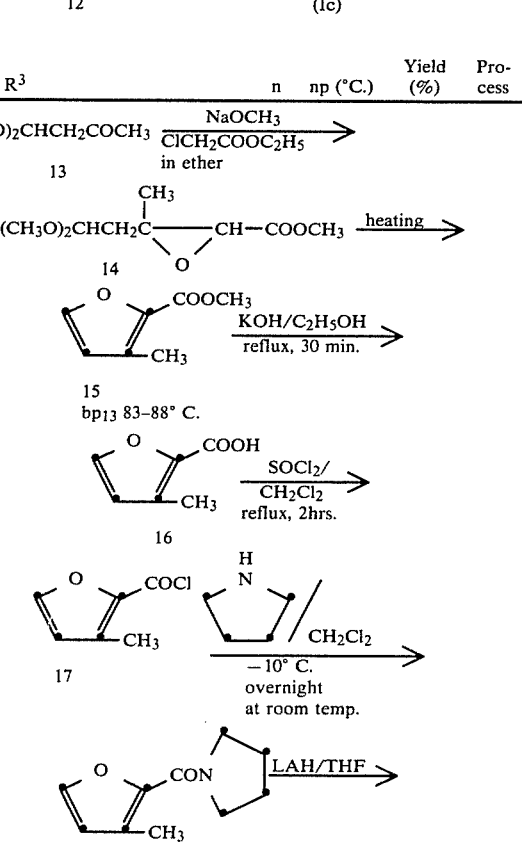

(CH₃O)₂CHCH₂COCH₃ →[NaOCH₃ / ClCH₂COOC₂H₅ in ether]

13

(CH₃O)₂CHCH₂C(CH₃)—CH—COOCH₃ (epoxide) →[heating]

14

⟨furan⟩-COOCH₃, CH₃ →[KOH/C₂H₅OH reflux, 30 min.]

15
bp$_{13}$ 83–88° C.

⟨furan⟩-COOH, CH₃ →[SOCl₂/ CH₂Cl₂ reflux, 2hrs.]

16

⟨furan⟩-COCl, CH₃ + H-N⟨pyrrolidine⟩ →[CH₂Cl₂ −10° C. overnight at room temp.]

17

⟨furan⟩-CON⟨pyrrolidine⟩, CH₃ →[LAH/THF]

18

-continued

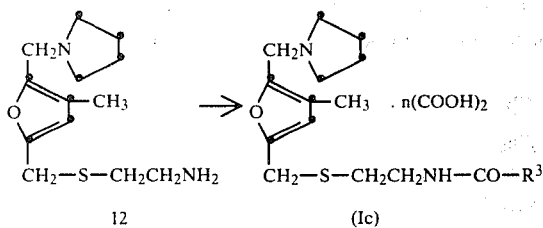

| | | 12 | | (Ic) | |
|---|---|---|---|---|---|

| Example No. | R³ | n | np (°C.) | Yield (%) | Process |
|---|---|---|---|---|---|

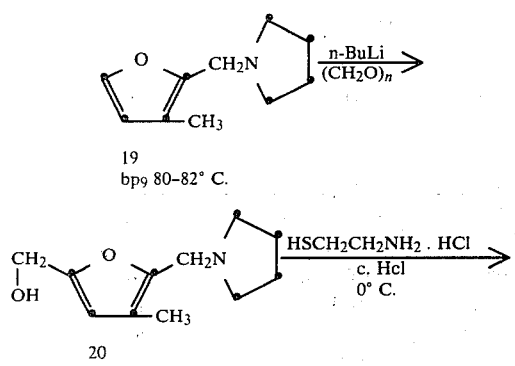

19
bp₉ 80–82° C.

20

[Org. Syn. Coll., 4,649; Brit. pat. 2,006,771]

EXAMPLES 46–49

The products (Id) are prepared from the following Compound 21 according to the respective methods:

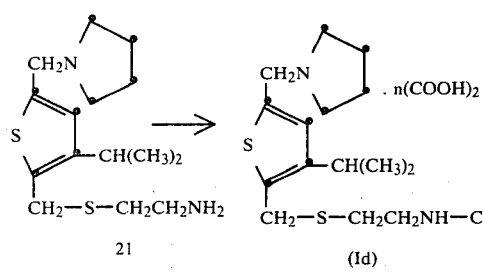

| Ex. No. | R³ | n | mp(°C.) | Yield (%) | Process |
|---|---|---|---|---|---|
| 46 | (pyridyl) | 1.5 | 149–152 d. | 80 | b |
| 47 | H— | 1 | 159–161 d. | 68.8 | c |
| 48 | CH₃OCO–(phenyl) | 1 | 172–174 d. | 78.7 | b |

-continued

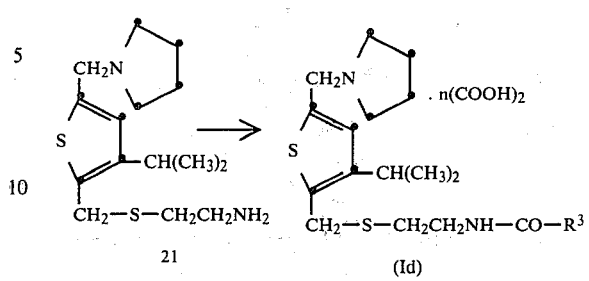

| | | 21 | | (Id) | |
|---|---|---|---|---|---|

| Ex. No. | R³ | n | mp(°C.) | Yield (%) | Process |
|---|---|---|---|---|---|
| 49 |  H₂NSO₂– | 1 | 195–197 d. | 56.5 | d |

Note:
Compound 21 is prepared according to the following route:

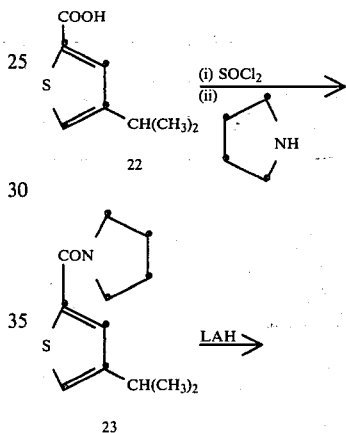

[J. Am. Chem. Soc., 77, 4066 ('55)]

24 bp₄ 109–112° C.

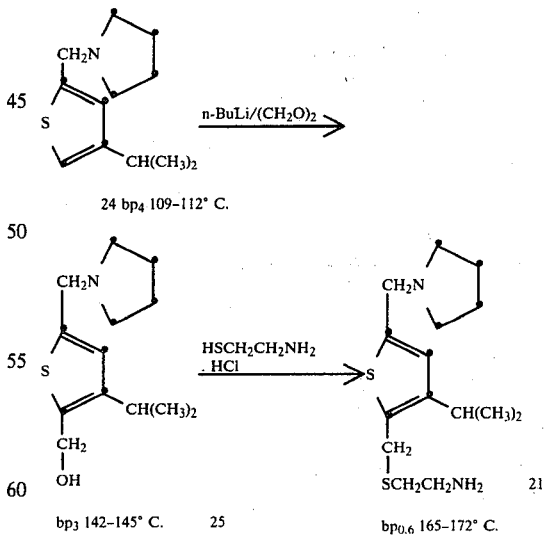

bp₃ 142–145° C.   25   bp₀.₆ 165–172° C.

EXAMPLES 50–53

The products (Ie) is prepared from the following Compound 26 according to the respective processes.

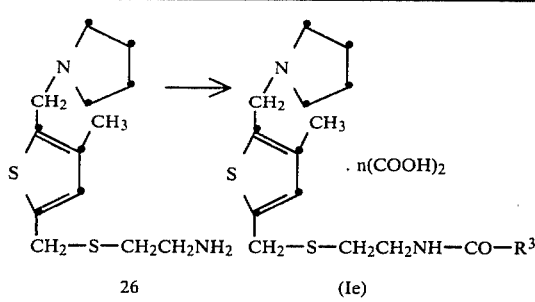

| Ex. No. | R³ | n | mp(°C.) | Yield (%) | Process |
|---|---|---|---|---|---|
| 50 | H | 1.5 | 150–153 d. | 86.5 | c |
| 51 | H₂NSO₂—⌬— | 0 | 111–113 | 29.4 | d |
| 52 | (pyridyl) | 1.5 | 155–157 d. | 84.2 | b |
| 53 | CH₃OCO—⌬— | 1 | 182–189 d. | 62.1 | b |

Note:
Compound 26 is prepared according to the following route:

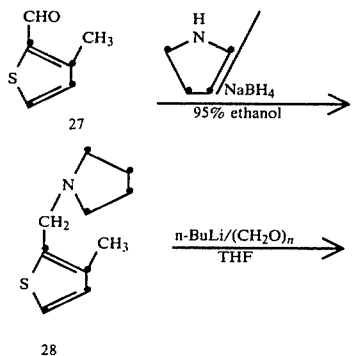

bp₂₅ 133–135° C.

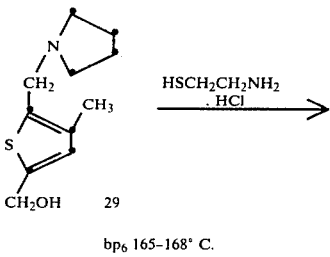

bp₆ 165–168° C.

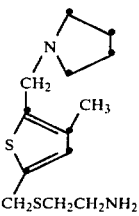

26   bp₀.₁ 145–150° C.

EXAMPLE 54

Preparation of N-[2-[[(5-dimethylaminomethyl-2-furyl)methyl]thio]ethyl]-4-hydroxyphenylacetamide:

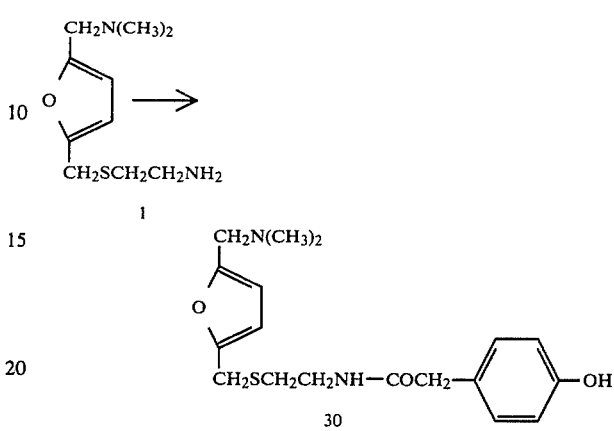

A suspension of Compound 1 (0.536 g), p-hydroxyphenylacetic acid (0.456 g) and DCC (0.619 g) in chloroform (15 ml) is stirred at room temperature for 48 hours. The reaction mixture is washed with water and the organic layer is dried and concentrated. The residue is purified by chromatography on a column of silica gel/methanol to give Compound 30 as an oil. The product is treated with oxalic acid/ethanol and then ether for crystallization to give the oxalate of Compound 30 (0.49 g). Yield is 41.2%. mp. 101°–103° C. (d.) (recrystallized from ethanol).

Anal. Calcd. for $C_{18}H_{24}N_2O_3S \cdot (COOH)_2 \cdot \frac{1}{2}H_2O$: C, 53.68; H, 6.08; N, 6.26; S, 7.16. Found: C, 53.99; H, 5.96; N, 6.03; S, 6.81.

Free base: NMR, $\delta CDCl_3$: 2.30 (6H), 3.45 (2H), 3.48 (2H), 6.10 (2H).

EXAMPLE 55

Compound 31 is prepared by reacting Compound 1 with monoethyl maleate and thionyl chloride in HMPA and acetonitrile.

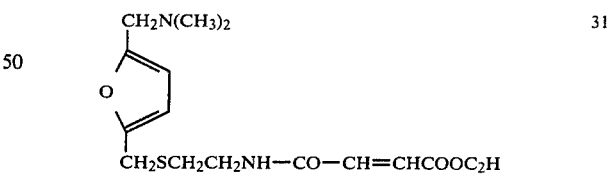

NMR, $\delta CDCl_3$: 1.30 (t., J=7, 3H), 2.27 (6H) 3.40 (2H) 3.70 (2H), 4.29 (q., J=7 Hz, 2H), 6.12 (2H), 6.83 (br., 2H).

The oxalate of Compound 31:
Anal. Calcd. for $C_{16}H_{24}N_2O_4S \cdot (COOH)_2$: C, 50.22; H, 6.09; N, 6.51; S, 7.43. Found: C, 50.04; H, 6.13; N, 6.40; S, 7.33.

EXAMPLE 56

Preparation of N-[2-[[[4-methyl-5-(1-pyrrolidinylmethyl)-2-furyl]methyl]thio]ethyl]-4-methoxycarbonylbenzamide:

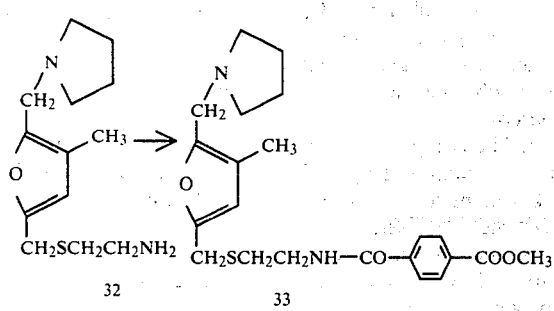

To a solution of Compound 32 (Brit. pat. 2,006,771) (400 mg) in pyridine (4 ml) is added methyl 4-(chloroformyl)-benzoate (357 mg) at −5° C. and the resultant mixture is allowed to stand at room temperature overnight. The reaction mixture is concentrated in vacuo and the residue is distributed between 5% aqueous sodium hydrogencarbonate and chloroform. The organic layer is washed with water, dried and concentrated. The residue is chromatographed on a column of silica gel/methanol to give Compound 33 (317 mg). Yield is 48%.

NMR, δCDCl$_3$: 1.95 (3H), 3.62 (2H), 3.70 (2H), 3.90 (3H), 6.02 (1H).

The mono-oxalate, mp. 164°–165° C.

Anal. Calcd. for $C_{24}H_{30}N_2O_8S$: C, 56.90; H, 5.97; N, 5.53; S, 6.33. Found: C, 56.62; H, 6.07; N, 5.56; S, 6.39.

EXAMPLES 57–61

The following products (If) are prepared from Compound 34 according to the acid chloride/pyridine method.

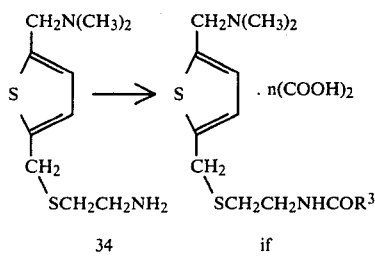

b.p. 0.8 148°–150° C. (Belg. pat. 867,105)

| Ex. No. | R$^3$ | n | mp (°C.) | Yield (%) |
|---|---|---|---|---|
| 57 | CH$_3$OCO—⟨◯⟩— | 1 | 178–179 d. | 80 |
| 58 | ⟨N◯⟩— | 2.5 | 150–152 | 82 |
| 59 | H | 1 | 114–116 | 80 |
| 60 | H$_2$NSO$_2$—⟨◯⟩— | 1 | 102–105 d. | 98 |
| 61 | ⟨◯⟩— | 1 | 142–144 | 62 |

EXAMPLES 62–67

Compounds (Ig) below are prepared from Compound 35.

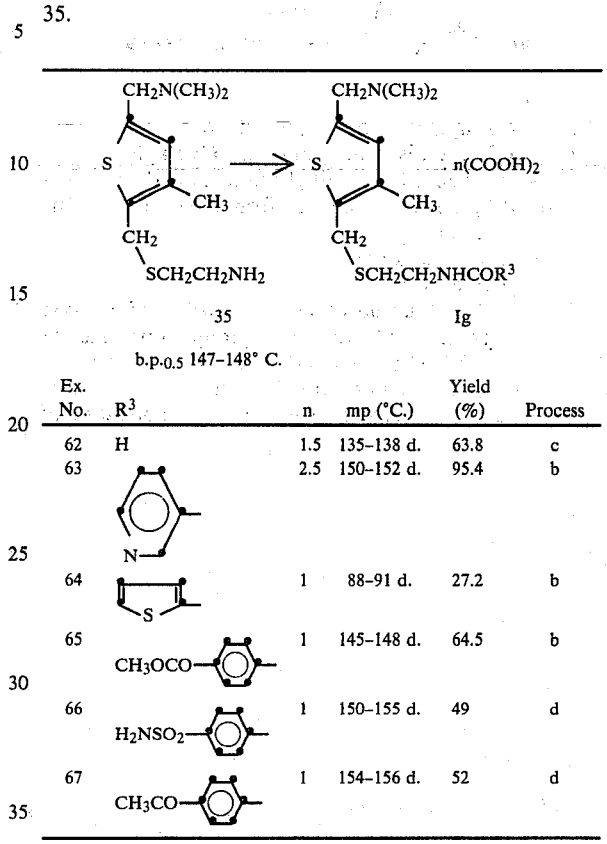

b.p.$_{0.5}$ 147–148° C.

| Ex. No. | R$^3$ | n | mp (°C.) | Yield (%) | Process |
|---|---|---|---|---|---|
| 62 | H | 1.5 | 135–138 d. | 63.8 | c |
| 63 | ⟨N◯⟩— | 2.5 | 150–152 d. | 95.4 | b |
| 64 | ⟨S◯⟩— | 1 | 88–91 d. | 27.2 | b |
| 65 | CH$_3$OCO—⟨◯⟩— | 1 | 145–148 d. | 64.5 | b |
| 66 | H$_2$NSO$_2$—⟨◯⟩— | 1 | 150–155 d. | 49 | d |
| 67 | CH$_3$CO—⟨◯⟩— | 1 | 154–156 d. | 52 | d |

EXAMPLES 68–70

The following products (Ih) are obtained from Compound 34 using the system of 2,2′-dipyridyl disulfide/triphenylphosphine/methylene chloride.

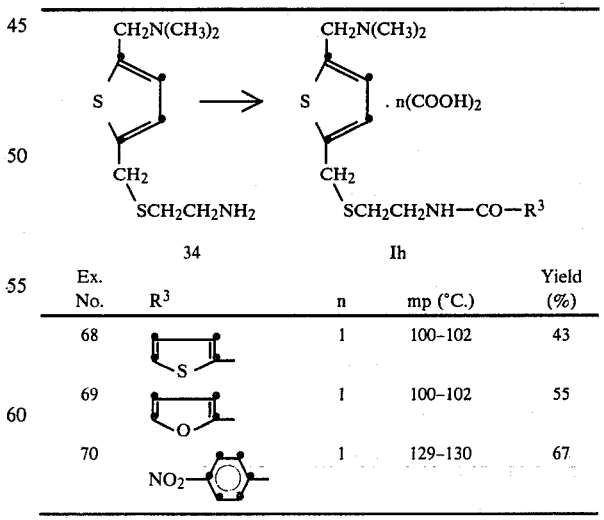

| Ex. No. | R$^3$ | n | mp (°C.) | Yield (%) |
|---|---|---|---|---|
| 68 | ⟨S◯⟩— | 1 | 100–102 | 43 |
| 69 | ⟨O◯⟩— | 1 | 100–102 | 55 |
| 70 | NO$_2$—⟨◯⟩— | 1 | 129–130 | 67 |

What we claim is:
1. A compound selected from the group consisting of a compound of the formula:

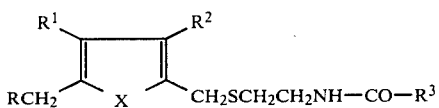

wherein
R is dimethylamino or 1-pyrrolidinyl;
$R^1$ and $R^2$ each is hydrogen or $C_1$–$C_3$ alkyl;
$R^3$ is hydrogen, $C_1$–$C_3$ alkyl unsubstituted or substituted by a member selected from the group consisting of cyano,
$C_1$–$C_3$ alkoxy and phenyl,
$C_3$–$C_6$ cycloalkyl,
$C_2$–$C_5$ alkenyl unsubstituted or substituted by one member selected from the group consisting of $C_1$–$C_3$ alkoxy, phenyl and phenoxy,
or $C_6$–$C_{10}$ aryl unsubstituted or substituted by one or two members selected from the group consisting of hydroxy, halogen, nitro, sulfamoyl, $C_1$–$C_3$ alkoxy, $C_1$–$C_3$ alkanoyl, $C_2$–$C_4$ alkoxycarbonyl, $C_2$–$C_4$ dialkylamino and $C_1$–$C_3$ alkanesulfonyl
and X is oxygen or sulfur
or a pharmaceutically acceptable acid addition salt thereof.

2. The compound according to claim 1, in which R is dimethylamino or pyrrolidinyl, $R^3$ is hydrogen, $C_1$–$C_3$ alkyl or phenyl unsubstituted or substituted by one or two members selected from the group consisting of hydroxy, halogen, sulfamoyl, $C_2$–$C_4$ alkoxycarbonyl, nitro, $C_1$–$C_3$ alkanoyl and methanesulfonyl, and X is oxygen or sulfur.

3. The compound according to claim 2, in which X is oxygen.

4. The compound according to claim 1 wherein R is dimethylamino, $R^3$ is phenyl substituted in the 4-position by sulfamoyl and X is oxygen.

* * * * *